US00RE38252E

(19) United States
(12) Reissued Patent
Cahoon et al.

(10) Patent Number: US RE38,252 E
(45) Date of Reissued Patent: Sep. 16, 2003

(54) CORN CDNA ENCODING SOUTHERN LEAF BLIGHT RESISTANCE

(75) Inventors: Rebecca E. Cahoon, Wilmington, DE (US); Guo-Hua Miao, Johnston, IA (US); J. Anotoni Rafalski, Wilmington, DE (US); Graziana Taramino, Wilmington, DE (US)

(73) Assignee: E.I. DuPont de Nemours & Company, Wilmington, DE (US)

(21) Appl. No.: 10/095,946

(22) Filed: Mar. 11, 2002

Related U.S. Patent Documents

Reissue of:
(64) Patent No.: 6,303,332
Issued: Oct. 16, 2001
Appl. No.: 09/183,959
Filed: Nov. 2, 1998

U.S. Applications:
(60) Provisional application No. 60/064,496, filed on Nov. 5, 1997.

(51) Int. Cl.[7] ..... C12P 21/06; C12Q 1/68; C12N 15/00; C12N 5/04; C07H 21/02

(52) U.S. Cl. ..... 435/69.1; 435/6; 435/320.1; 435/419; 536/23.4; 536/24.33; 536/23.1; 436/94

(58) Field of Search ..... 435/69.1, 6, 320.1, 435/419; 536/23.1, 23.4, 24.33; 436/94

(56) References Cited

FOREIGN PATENT DOCUMENTS

| | | |
|---|---|---|
| WO | WO 98/04586 A1 | 2/1998 |
| WO | WO 00/01721 A1 | 1/2000 |
| WO | WO 00/01722 A2 | 1/2000 |

OTHER PUBLICATIONS

R. Bueschges et al.: "The Barley MLO Gene: A Novel Control Element of Plant Pathogen Resistor" Cell, vol. 88, No. 5, Mar. 7, 1997, pp. 695–705, XP002035301, pp. 695, 697, 698, 701; Fig. 2.

T. Newman et al.: "Genes Galore: A Summary of Methods for Assessing Results from Large–scale Partial Sequencing of Anonymous Arabidopsis cDNA Clones" EMBL Sequence Data Library, Jun. 27, 1994, XP002095686, Heidelberg Germany, Accession No. T22145.

N. Kaplan, et al., "Sequence FA. Thaliana BAC T10P11 from Chromosome IV–Unpublished" Embl Sequence Data Library, Jul. 23, 1997, XP002095687, Heidelberg, Germany, Accession No. AC002330.

G. Simons et al., "AFLP–Based Fine Mapping of the MLO to a 30–KB DNA Segment of the Barley Genome" Genomics, vol. 44, No. 1, Jan. 1997, pp. 64–70, XP002049472.

Smith and Hooker, Crop Science, 13, 330–331, 1973, Monogenic Chlorotic–Lesion Resistance in Corn to *Helminthosporium maydis*.

Hammond–Kosack, K.E. and Jones, J.D.G., Ann Rev. Plant Phusiot. Mol. Bio., 48, 575–607, 1997, Plant Disease Resistance Genes.

Wang, G.L. et al., Mol. Plant–Microbe Interact., 9(9), 850–855, 1996, The Cloned Gene, Xa21, Confers Resistance to Multiple Xanthomonas Oryzae pv. oryzae Isolates in Transgenic Plants.

Buschges, R. et al., Cell, 88, 695–705, 1997, The Barley Mlo Gene: A Novel Control Element of Plant Pathogen Resistance.

Craig. J. and Fagemisin, J.M., Plant Dis. Rep. 53, 742–743, 1969, Inheritance of Chlorotic Lesion Resistance to *Helminthosporium maydis* in Maize.

Craig and Daniel–Kalio, Plant Disease Reporter, 52, No. 2, 134–136, 1968, Chlorotic Lesion Resistance to *Helminthosportum maydis* in Maize.

Fromm et al., Bio/Technology, 8, 833–839, 1990, Inheritance and expression of Chimeric Genes in the Progeny of Transgenic Maize Plants.

National Center for Biotechnology Information gi Accession No. 2765817, Jan. 8, 1998, Panstruga, R.

National Center for Biotechnology Information gi Accession No. 2252632, Aug. 4, 1997, Rounsley et al., *Arabidopsis thaliana* BAC T19D16 Genomic Sequence.

National Center for Biotechnology Information gi Accession No. 2459447, Oct. 8, 1997, Rounsley et al., *Arabidopsis thaliana* BAC T19D16 F2P9 Genomic Sequence.

National Center for Biotechnology Information gi Accession No. 1877221, Mar. 7, 1997, Buschges et al., The Barley Mlo Gene: A Novel Control Element of Plant Pathogen Resistance.

*Primary Examiner*—Ali R. Salimi

(57) ABSTRACT

This invention relates to an isolated nucleic acid fragment encoding a $SCLB^R$ protein. The invention also relates to the construction of a chimeric gene encoding all or a portion of the $SCLB^R$ protein, in sense or antisense orientation, wherein expression of the chimeric gene results in production of altered levels of the $SCLB^R$ protein in a transformed host cell.

11 Claims, 1 Drawing Sheet

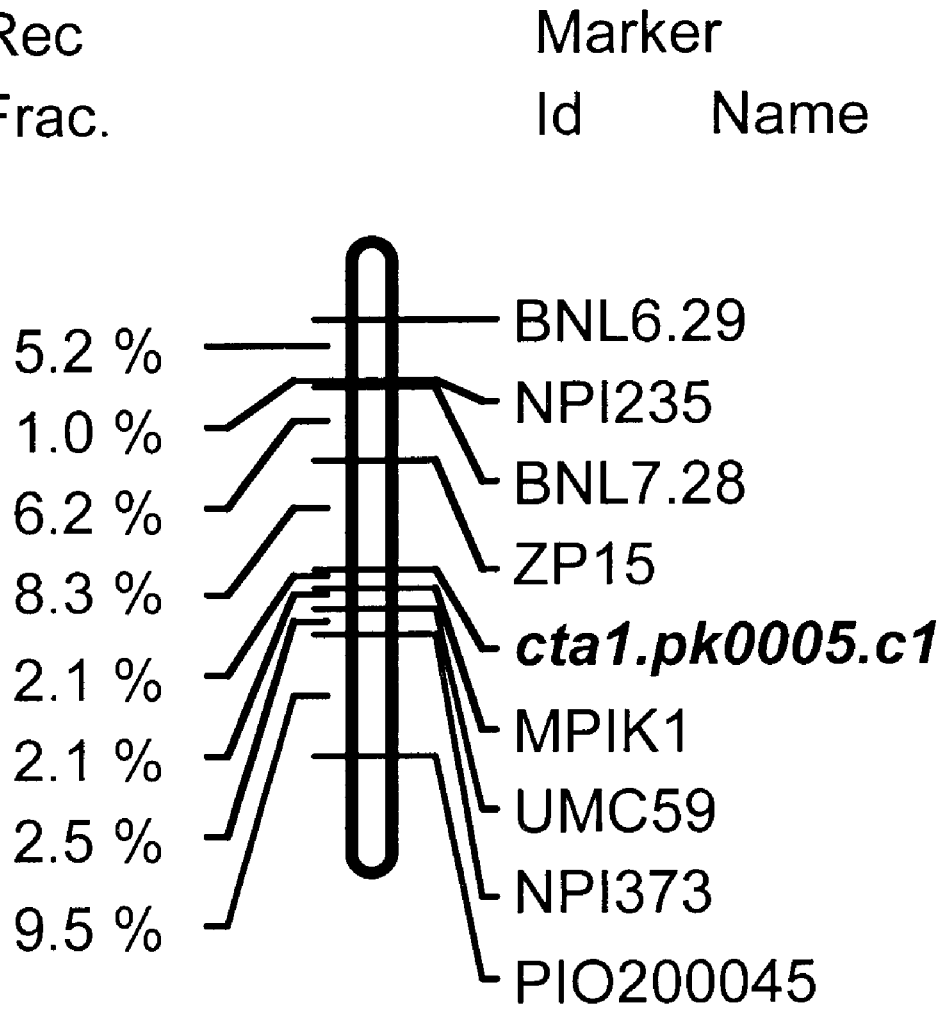
FIG. 1 NEW

CORN CDNA ENCODING SOUTHERN LEAF BLIGHT RESISTANCE

Matter enclosed in heavy brackets [ ] appears in the original patent but forms no part of this reissue specification; matter printed in italics indicates the additions made by reissue.

[This application claims the benefit of U.S. Provisional Application No. 60/064,492, filed Nov. 5, 1997. This is a provisional application No. 60/064,492 filed Nov. 5, 1997 now abandoned.]*This application is a reissue of application No. 09/183,959 filed Nov. 2, 1998, now U.S. Pat. No. 6,303,332 which claims the benefit of provisional application No. 60/064,492 filed Nov. 5, 1997.*

FIELD OF THE INVENTION

This invention is in the field of plant molecular biology. More specifically, this invention pertains to nucleic acid fragments encoding proteins involved in corn (Zea mays) resistance to Southern corn leaf blight disease, caused by the fungus Helminthosporium maydis.

BACKGROUND OF THE INVENTION

Southern or Maydis Leaf Blight is a serious disease of corn caused by Helminthosporiurn maydis Nisik. (Cochliobolits heterostrophus (Drechs)). While corn hybrids with normal cytoplasm are resistant to Race T of the pathogen, Race O shows no differential reaction between plants with different cytoplasms; however, sources of resistance are available (Shurtleff (1973) Compendium of Corn Diseases). Chlorotic lesion resistance to Race 0 was identified in an East African line of corn (Jeweus and Daniel-Kalio (1968) Plant Dis Rep. 53:134–136). The resistant plants inhibit fungal sporulation and are distinguished by the presence of small chlorotic lesions. Significantly, the resistance is recessive (Smith and Hooker (1973) Crop Science 13:330–331). It was reported that disease is controlled by two linked recessive genes.

It is well established that resistance to many diseases in plants is mediated by the interaction of plant genes referred to as "R" genes with corresponding Avr genes expressed by the pathogen (Hammond-Kosack, K. E. and Jones, J. D. G. (1997) Ann Rev. Plant Phusiol Plant Mol. Bio. 48:1–39). This interaction leads to the activation of plant responses which in turn results in increased resistance to disease. This resistance is frequently mediated by the "hypersensitive response", a localized cell death phenomenon that occurs in the areas of plant tissue invaded by the pathogen. This AvrlR interaction is race-specific; i.e., particular alleles of the plant R gene respond only to specific races of the pathogen which express a corresponding Avr gene (Flor, H. (1971) Ann. Rev. Phytophatol, 9:275–296). Most of the R genes characterized to date are dominant; i.e., resistance is exhibited by plants carrying the appropriate R allele in either an heterozygous or homozygous state. Some R genes have been isolated by map-based cloning. Many homologs of R genes have also been identified by sequence similarity. Because of the rapid evolution of plant resistance to disease, homology of a CDNA or genomic DNA sequence to a known R gene from a different plant species does not allow one to predict the pathogen specificity of that particular R gene. No general methods for such prediction exist today.

Genes involved in resistance of plants to plant pathogens may be used to engineer disease resistance into plants normally sensitive to disease using several different approaches. Transgenic plants containing alleles of R genes demonstrate resistance to corresponding races of the pathogen (Wang, G.-L. et al. (1996) Mol. Plant-Microbe Interact. 9(9):850–855). The resistance genes may also be engineered to respond to non-naive signals derived from the pathogen. In addition, pathogen-derived Avr genes may be expressed in a controlled manner in plants to strengthen the response to a pathogen. Genes further downstream from the R genes in the signal transduction pathways that transmit signals to the disease response effector genes may be engineered to directly respond to pathogen infection, thereby shortening the response pathway.

The process of the hypersensitive response to a pathogen, and the signaling networks involved, are poorly understood. In no case have all of the genes involved in transmitting the signal from the pathogen to the site of the initiation of the hypersensitive response been identified.

In a few cases, the functioning of a disease resistance mechanism different from the Avr/R interaction described above results in a recessive, rather than dominant pattern of resistance. One such example is the Mlo gene of barley, which conveys resistance to Erysiphe graminis f. sp. hordei. The barley gene has been recently isolated by a positional cloning approach (Bueschges, R. et al. (1997) Cell 88:695–705). The dominant (sensitive) allele (Mlo) is thought to encode a protein involved in regulation of leaf cell death and in the onset of pathogen defense. The partial or complete inactivation of Mlo results in the priming of the disease-resistance response even in the absence of the pathogen, and leads to increased resistance to E. graminis.

The available scientific data concerning Mlo-mediated disease resistance in barley points towards another approach to controlling disease: priming the pathogen response pathway by diminishing the effectiveness of negative regulation of the hypersensitive response. Appropriately engineered plants may show increased pathogen resistance at the expense of expressing some pathogen response-related genes even in the absence of pathogen. Sense or antisense inhibition or targeted gene disruption of Mlo and Mlo-related genes may have such an effect. Resistance to other pathogens may also be increased using this approach.

Mlo-related cDNA clones and DNA segments of genomic DNA, and their homologs and derivatives, may also be used as molecular probes to track inheritance of corresponding loci in genetic crosses, and thus facilitate the plant breeding process. Moreover, these DNA sequences may also be used as probes to isolate, identify and genetically map Mlo and other closely related disease resistance genes.

SUMMARY OF THE INVENTION

The instant invention relates to isolated nucleic acid fragments encoding a corn homolog of the barley Mto protein. Specifically, the instant invention relates to isolated nucleic acid fragments encoding plant proteins involved in the regulation of plant cell death response in corn which, surprisingly, is associated with resistance of corn to Southern corn leaf blight disease caused by the fungus Helminthosporium maydis. In addition, this invention relates to nucleic acid fragments that are complementary to nucleic acid fragments encoding a corn homolog of the barley Mlo protein. The corn homolog of the barley Mlo gene and corresponding protein will hereinafter be referred to as the putative Southern corn leaf blight Resistance of $SCLB^R$ gene or protein, respectively.

An additional embodiment of the instant invention pertains to a polypeptide encoding all or a substantial portion of a $SCLB^R$ protein.

In another embodiment, the instant invention relates to a chimeric gene that comprises a nucleic acid fragment encoding the $SCLB^R$ protein or to a chimeric gene that comprises a nucleic acid fragment that is complementary to the nucleic acid fragment encoding the $SCLB^R$ protein, operably linked to suitable regulatory sequences, wherein expression of the chimeric gene results in production of levels of a $SCLB^R$ protein in transformed host cells that are altered (i.e., increased or decreased) from the levels produced in untransformed host cells.

In a further embodiment, the instant invention concerns a transformed host cell comprising in its genome a chimeric gene encoding a $SCLB^R$, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a $SCLB^R$ protein in a transformed host cell comprising: a) transforming a host cell with a chimeric gene comprising a nucleic acid fragment encoding a $SCLB^R$ protein; and b) growing the transformed host cell under conditions that are suitable for expression of the chimeric gene wherein expression of the chimeric gene results in production of altered levels of $SCLB^R$ protein in the transformed host cell.

An addition embodiment of the instant invention concerns a method for obtaining a nucleic acid fragment encoding all or a substantial portion of an amino acid sequence encoding a $SCLB^R$ protein.

A further embodiment of the instant invention concerns a method for using the instant nucleic acid fragments and their homologs and derivatives as molecular probes to monitor inheritance of corresponding loci in genetic crosses, and thus to facilitate and accelerate plant breeding. Additionally, the instant nucleic acid fragments may be used as probes to isolate, identify and genetically map $SCLB^R$ and other closely related disease resistance genes.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIG. [1A and FIG. 1B ] *1* is a genetic map of chromosome 6 of corn, including the position of cDNA clone cta1.pk0005. c1. The map was constructed using Mapmaker 3.0 for the Macintosh (Lander, E. S. et al. (1987) Genomics 1:174–181) and mapping data from Burr et al. (Burr et al. (1988) Genetics 118:519–526).

FIG. 2A and FIG. 2B is an alignment of nucleotides 781 to 1390 of the contig assembled with the nucleotide sequence of cDNA insert in clone cta1.pk0005.c1 and the 5' RACE product obtained using PCR primer P3 (SEQ ID NO:9) with the sequences of the 703 bp (SEQ ID NO:17) product obtained by PCR amplification of corn genomic DNA using primers P1 and P2. The intent of the intron sequences is indicated with an arrow. Intron sequences are shown in lowercase. The gt/ag invariant intron boundary sequences are bold and underlined.

FIG. 3A and FIG 3B is an alignment of nucleotides 60 to 520 from the sequence of cDNA Mlo3b3 (SEQ ID NO:11) with the sequence of the 765 bp (SEQ ID NO:18) product obtained by PCR amplification of corn genomic DNA using primers P1 and P2. The extent of the intron sequences is indicated with an arrow. Intron sequences are shown in lowercase. The gt/ag invariant intron boundary sequences are bold and underlined.

The following sequence descriptions and Sequence Listing attached hereto comply with the rules governing nucleotide and/or amino acid sequence disclosures in patent applications as set forth in 37 C.F.R. §1.821–1.825.

SEQ ID NO:1 is the nucleotide sequence comprising the entire cDNA insert in clone cc3. pk0007. g3 encoding an almost full-length $SCLB^R$ protein.

SEQ ID NO:2 is the deduced amino acid sequence of an almost full-length $SCLB^R$ protein derived from the nucleotide sequence of SEQ ID NO:1.

SEQ ID NO:3 is the nucleotide sequence comprising a portion of the cDNA insert in clone cr1n.pk0154.a3 encoding the C-terminal half of a $SCLB^R$ protein.

SEQ ID NO:4 is the deduced amino acid sequence of the C-terminal half of a $SCLB^R$ protein derived from the nucleotide sequence of SEQ ID NO:3.

SEQ ID NO:5 is the nucleotide sequence comprising a portion of the cDNA insert in clone cs1.pk0071.e3 encoding the C-terminus of a $SCLB^R$ protein.

SEQ ID NO:6 is the deduced amino acid sequence of the C-terminus of a $SCLB^R$ protein derived from the nucleotide sequence of SEQ ID NO:5.

SEQ ID NO:7is the nucleotide sequence comprising the entire CDNA insert in clone cco1.pk0052.b10 encoding a full-length $SCLB^R$ protein.

SEQ ID NO:8is the deduced amino acid sequence of a full-length $SCLB^R$ protein derived from the nucleotide sequence of SEQ ID NO:7.

SEQ ID NO:9 is the nucleotide sequence comprising a contig assembled from the entire cDNA insert in clone cta1.pk0005.c1 and the 5' RACE PCR product obtained using PCR primer P3 encoding a full-length $SCLB^R$ protein.

SEQ ID NO:10 is the deduced amino acid sequence of a full-length $SCLB^R$ protein derived from the nucleotide sequence of SEQ ID NO:9.

SEQ ID NO:11 is the nucleotide sequence comprising Mlo3b3, the 3' RACE PCR product obtained using clone cta1.pk0005.c1 and PCR primer P1, encoding a fragment of a $SCLB^R$ protein.

SEQ ID NO:12 is the deduced amino acid sequence of a fragment of a $SCLB^R$ protein derived from the nucleotide sequence of SEQ ID NO:11.

SEQ ID NO:13 is the nucleotide sequence comprising a portion of the cDNA insert in clone cen3n.pk0062.b7 encoding a fragment of a $SCLB^R$ protein.

SEQ ID NO:14 is the deduced amino acid sequence of a fragment of a $SCLB^R$ protein derived from the nucleotide sequence of SEQ ID NO:13.

SEQ ID NO:15 is the nucleotide sequence of PCR primer P1.

SEQ ID NO:16 is the nucleotide sequence of PCR primer P2.

SEQ ID NO:17 is the nucleotide sequence of the 703 bp PCR product obtained by amplification of corn genomic DNA using PCR primers P1 and P2.

SEQ ID NO:18, is the nucleotide sequence of the 765 bp PCR product obtained by amplification of corn genomic DNA using PCR primers P1 and P2.

SEQ ID NO:19 is the nucleotide sequence of PCR primer P3.

SEQ ID NO:20 is the nucleotide sequence of PCR primer P4.

The Sequence Listing contains the one letter code for nucleotide sequence characters and the three letter codes for amino acids as defined in conformity with the IUPACI-UBMB standards described in Nucleic Acids Research 13:3021–3030 (1985) and in the Biochemical Journal 219 (No. 2):345–373 (1984) which are herein incorporated by reference. Tile symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. As used herein, "contig" refers to an assemblage of overlapping nucleic acid sequences to form one contiguous nucleotide sequence. For example, several DNA sequences can be compared and aligned to identify common or overlapping regions. The individual sequences can then be assembled into a single contiguous nucleotide sequence.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes, which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes the substantially similar nucleic acid sequences encompassed by this invention are also defined by their ability to hybridize, under stringent conditions (0.1×SSC, 0.1% SDS, 65° C.), with the sequences exemplified herein. Preferred substantially similar nucleic acid fragments of the instant invention are those nucleic acid fragments whose DNA sequences are 80% identical to the coding sequence of the nucleic acid fragments reported herein. More preferred nucleic acid fragments are 90% identical to the coding sequence of the nucleic acid fragments reported herein. Most preferred are nucleic acid fragments that are 95% identical to the coding sequence of the nucleic acid fragments reported herein.

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) J. Mol. Biol.215:403–410 [; see also www.ncbi.nlm.nih.giv/BLAST/]). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the $SCLB^R$ protein as set forth in SEQ ID NOs:2, 4, 6, 8, 10, 12 and 14. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) Biochemistry of Plants 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) Molecular Biotechnology 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) Plant Cell 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,23 1,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) Ann. Rev. Plant Phys. Plant Mol. Biol. 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) Plant Phys. 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) Meth. Enzymol.(143:277) and particle-accelerated or "gene gun" transformation technology (Klein et al. (1987) Nature (London) 327:70–73; U.S. Pat. No. 4,945,050, incorporated herein by reference).

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Press: Cold Spring Harbor, 1989 (hereinafter "Maniatis").

Nucleic acid fragments encoding at least a portion of several corn homologs of the barley Mlo protein have been isolated and identified by comparison of random plant cDNA sequences to public databases containing nucleotide and protein sequences using the BLAST algorithms well known to those skilled in the art. These nucleic acid fragments encode plant proteins involved in the regulation of plant cell death response in corn which, surprisingly, is associated with resistance of corn to souther corn leaf blight disease caused by the fungus Helminthosporium maydis. Table 1 lists the designation of the cDNA clones that comprise the nucleic acid fragments encoding $SCLB^R$ proteins.

TABLE 1

Corn Homologs of Barley Mlo Protein

| Enzyme | Clone | Plant |
|---|---|---|
| $SCLB^R$ protein | cc3.pk0007.g3 | corn |
| | cco1.pk0052.b10 | corn |

TABLE 1-continued

Corn Homologs of Barley Mlo Protein

| Enzyme | Clone | Plant |
|---|---|---|
| | cen3n.pk0062.b7 | corn |
| | cr1n.pk0154.a3 | corn |
| | cs1.pk0071.e3 | corn |
| | cta1.pk0005.c1 | corn |
| | mlo3b3 | corn |

The homology with the barley Mlo protein indicated that these cDNAs corresponded to genes involved in disease resistance, but did not provide information as to the possible disease specificity in corn; Erysiphe graminis, the causative agent of powdery mildew in barley, is not a pathogen of corn. Ultimately, disease specificity information was provided by genetic mapping experiments.

PCR amplification of maize genomic DNA using two primers, P1 and P2, designed using the nucleic acid sequence of CDNA clone cta1.pk0005. c1. resulted in the amplification of two DNA segments, both homologous to ctal .pk0005.c1. but differing in the numbers of introns (see Example 4). Genetic mapping experiments (see Example 5) placed one of the two genomic segments on chromosome 6, in Bin 6.01, between markers BNL7.28 and UMC59. Three disease resistance loci map to the same bin on chromosome 6:Maize dwarf mosaic virus (MDMV), wheat streak mosaic virus (WSMV) and Southern corn leaf blight (SCLB). Of the three disease resistance loci, the SCLB locus is unique in that it is the only known recessive disease resistance locus in corn. Therefore, it is highly likely that the Mlo homolog represented by the 765 bp amplification product containing three introns corresponds to the Southern corn leaf blight resistance ($SCLB^R$) gene. The second genomic sequence, which contains two introns, is likely to be a second, linked $SCLB^R$ gene. The existence of two linked genes has been reported by Craig and Fajeminsin (Craig, J. and Fagemisin, J. M (1969) Plant Dis. Rep.53:742–743).

The nucleic acid fragments of the instant invention may be used to isolate cDNAs and genes encoding homologous $SCLB^R$ proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other $SCLB^R$ proteins, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) Proc. Natl. Acad. Sci. USA 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) Proc. Natl. Acad. Sci USA 86:5673; Loh et al., (1989) Science 243:217). Products generated by the 3' and 5' RACE procedures can be combined to generate full-length cDNAs (Froliman, M. A. and Martin, G. R., (1989) Techniques 1:165).

Availability of the instant nucleotide and deduced amino acid sequences facilitates immunological screening of CDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen CDNA expression libraries to isolate full-length CDNA clones of interest (Lemer, R. A. (1984) Adv. Immunol.36:1; Maniatis).

The nucleic acid fragments of the instant invention may be used to create transgenic plants in which the disclosed $SCLB^R$ proteins are present at higher or lower levels than normal or in cell types or developmental stages in which they are not normally found. This would have the effect of altering the level of $SCLB^R$ in those cells, and thus changing the ability of corn to resist certain diseases.

Overexpression of the $SCLB^R$ proteins of the instant invention may be accomplished by first constructing a chimeric gene is which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) EMBO J.4:2411–2418; De Almeida et al., (1989) Mol Gen. Genetics 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant $SCLB^R$ gene product to different cellular compartments, or to facilitate its secretion from the cell. It is thus envisioned that the chimeric gene described above may be further supplemented by altering the coding sequence to encode $SCLB^R$ proteins with appropriate intracellular targeting sequences such as transit sequences (Keegstra, K. (1989) Cell 56:247–253), signal sequences or sequences encoding endoplasmic reticulum localization (Cluispeels, J. J., (1991) Ann. Rev. Plant Phys. Plant Mol Biol.42:21–53), or nuclear localization signals (Raikhel, N. (1992) Plant Phys. 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding $SCLB^R$ proteins in plants for some applications. In order to accomplish this, a chimeric gene designed for co-suppression of the instant $SCLB^R$ protein can be constructed by linking a gene or gene fragment encoding an $SCLB^R$ protein to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

For example, the instant nucleic acid fragments may be combined in sense or antisense orientation with a suitable plant expression vector comprising a strong plant promoter sequence and plant terminator sequences. The recombinant vector may then be introduced into plants by transformation using techniques well known to those skilled in this art. Some of the transgenic plants recovered from the transformation process will exhibit diminished expression of the gene corresponding to the instant nucleic acid fragments. These plants may be identified by Northern blot analysis. These individuals may then be tested for disease resistance, and resistant individuals recovered for future use as a source of genetically controlled resistance in plant breeding schemes. Longer cDNA clones, especially ctal.pk0005.c1. cc3.pk0007.g3 and cco1.pk0052.b10 are preferred. cDNA clones cs1.pk0071.e3, cr1n.pk0154.a3, mlo3b3 and cen3n.pk0062.b7 may also be used in a similar way to inhibit expression of their corresponding genes.

The instant $SCLB^R$ protein (or portions thereof) may be produced in heterologous host cells, particularly in the cells of microbial hosts, and can be used to prepare antibodies to the these proteins by methods well known to those skilled in the art. The antibodies are useful for detecting $SCLB^R$ protein in situ in cells or in vitro in cell extracts. Preferred heterologous host cells for production of the instant $SCLB^R$ protein are microbial hosts. Microbial expression systems and expression vectors containing regulatory sequences that direct high level expression of foreign proteins are well known to those skilled in the art. Any of these could be used to construct a chimeric gene for production of the instant $SCLB^R$ protein. This chimeric gene could then be introduced into appropriate microorganisms via transformation to provide high level expression of the encoded $SCLB^R$ protein.

An example of a vector for high level expression of the $SCLB^R$ protein in a bacterial host is provided (Example 8).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) or restriction-digested plant genomic DNA may be probed with the nucleic acid fragments of the instant invention. The resulting banding patterns may then be subjected to genetic analyses using computer programs such as MapMaker (Lander et at., (1987) Genomic, 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) Am. J. Hum. Genet. 32:314–331).

The production and use of plant gene-derived probes for use in genetic mapping is describe din R. Bernatzky, R. and Tanksley, S. D. (1986) Plant Mol. Biol. Reporter 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: Nonmammalian Genomic Analysis. A Practical Guide, Academic press 1996, pp. 319–346, and references cited therein).

In another embodiment, nucleic acid probes derived from the instant nucleic acid sequences may be used in direct fluorescence in situ hybridization (FISH) mapping (Trask, B. J. (1991) Trends Genet.7:149–154). Although current methods of FISH mapping favor use of large clones (several to several hundred KB; see Laan, M. et al. (1995) Genome Research 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) J. Lab. Clin. Med.114(2):95–96), polymorphism of PCR-amplified fragments (CAPS; Sheffield, V. C. et al. (1993) Genomics 16:325–332), allele-specific ligation (Landegren, U. et al. (1988) Science 241:1077–1080), nucleotide extension reactions (Sokolov, B. P. (1990) Nucleic Acid Res.18:3671), Radiation Hybrid Mapping (Walter, M. A. et al. (1997) Nature Genetics 7:22–28) and Happy Mapping (Dear, P. H. and Cook, P. R. (1989) Nucleic Acid Res 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

For example, genetic diagnostics of the southern corn leaf blight (SCLB), maize dwarf mosaic virus (MDMV), wheat streak mosaic virus (WSMV) loci, and of other lock corresponding or tightly linked to cta1.pk0005.c1 and related cDNAs may be performed. Knowledge and availability of the nucleotide sequences corresponding to the corn Mlo homolog embodies by CDNA clone cta1.pk0005.c1 allows one skilled in the art to use one of many generally known techniques, like restriction fragment length polymorphism, allele specific PCR, single strand conformational polymorphism, allele-specific ligation. Cleaved Amplified Polymorphic Fragments (CAPS) and other similar methods discussed above and known to those skilled in the art, to follow the inheritance of a particular allele in genetic crosses during the process of plant breeding. Through this process, the plant carrying the alleles conferring disease resistance may be always recovered reliably.

For example, the 765 bp PCR fragment, which is produced only from the CM37 genotype and not from the T232 genotype using primers designed from the nucleotide sequence of cDNA clone cta1.pk0005.c1. is therefore polymorphic between these two genotypes and could be used to follow inheritance of the allele corresponding to the 765 bp PCR fragment in crosses of CM37 and T232, and in any crosses with a genotype which does not produce the 765 bp fragment in the above described PCR process.

Loss of function mutant phenotypes may be identified for the instant cDNA clones either by targete gene disruption protocols or by identifying specific mutants for these genes contained in a maize population carrying mutation in all possible genes (Ballinger and Benzer, (1989) Proc. Natl. Acad. Sci USA 86:9402; Koes et al., (1995) Proc. Natl. Acad. Sci USA 92:8149; Bensen et al., (1995) Plant Cell 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, slipra). The amplification of a specific DNA fragment with these primers indicates the insertion of the mutation tag element in or near the plant $SCLB^R$ gene. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous $SCLB^R$ gene can be identified and obtained. This mutant plant can then be used to determine or confirm the natural function of the $SCLB^R$ gene product.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of CDNA Libraries, Isolation and Sequencing of cDNA clones CDNA libraries representing mRNAs from various corn tissues were prepared. The characteristics of the libraries are described below.

TABLE 2 cDNA Libraries from Corn

| Library | Tissue | Clone |
|---|---|---|
| cc3 | Corn Callus Embryo | cc3.pk0007.g3 |
| cco1 | Corn Cob of 67 Day Old Plants Grown in Green House | cco1.pk0052.b10 |
| cen3n | Corn Endosperm 20 Days After Pollination* | cen3n.pk0062.b7 |
| cr1n | Corn Root From 7 Day Old Seedlings* | cr1n.pk0154.a3 |
| cs1 | Corn Silk | cs1.pk0071.e3 |
| cta1 | Corn Tassel | cta1.pk0005.c1 |

*These libraries were normalized essentially as described in U.S. Pat. No. 5,482,845, incorporated herein by reference.

cDNA libraries were prepared in Uni-ZAP™ XR vectors according to the manufacturer's protocol (Stratagene Cloning Systems, La Jolla, Calif.). Conversion of the Uni-ZAP™ XR libraries into plasmid libraries was accomplished according to the protocol provided by Stratagene. Upon conversion, cDNA inserts were contained in the plasmid vector pBluescript, CDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags of "ESTs"; see Adams, M. D. et al., (1991) Science 252:1651). The resulting ESTs were analyzed using a Perkin Elmer Model 377 fluorescent sequencer.

Example 2

Identification of cDNA Clones

ESTs encoding SCLB$^R$ proteins were identified by conducting BLAST (Basic Local Alignment Search Tool; Altschul, S. F., et al., (1993) J. Mol. Biol.215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN° FN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) Nature Genetics 3:266–272) provided by the NCBI. For convenience, the P-value (probability) of conserving match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding SCLB$^R$ Proteins

The BLASTX search using the nucleotide sequences from clones cen3n.pk0062.b7, cs1.pk0071 .e3, cc3.pk0007.g3 and cta1. pk0005.c1 revealed similarity of the proteins encoded by the cDNAs to the barley mlo gene (NCBI gi Accession No. 1877221). The BLASTX results for each of these ESTs are shown in Table 3:

TABLE 3

BLASTX Results for Clones Encoding Polypeptides Homologous to Barley Mlo Protein

| Clone | BLAST pLog Score 1877221 (barley) |
|---|---|
| cen3n.pk0062.b7 | 73.04 |
| cs1.pk0071.e3 | 9.30 |
| cc3.pk0007.g3 | 15.77 |
| cta1.pk0005.c1 | 53.89 |

Further BLASTX analyses were performed which revealed that these ESTs and sequences from other clones contained similarities to putative Arabidopsis thaliana Mlo homologs found in the NCBI database. BLASTX search using the nucleotide sequences from clones cc3.pk0007.g3, cr1n.pk0154.a3 and cs1.pk0071.e3 revealed similarity to the Arabidopsis thaliana AtMlo-h1 protein (NCBI gi Accession No. 2765817). BLASTX search using the nucleotide sequences from clone cco1.pk0052.b10 revealed similarity to the Barley Mlo protein isolog from Arabidopsis thaliana (NCBI gi Accession No. 2252632). The BLASTX searchs using (i) the nucleotide sequences from the contig assembled of the entire cDNA sequence in clone cta1.pk0005.c1 and the 5' RACE product obtained using Marathon™ cDNA amplification kit (Clontech catalog No. K1802-1) with PCR primer P3 and (ii) using the nucleotide sequence from mlo3b3, and 3' RACE product from clone cta1.pk0005.c1 obtained using Marathon™ cDNA amplification kit (Clontech catalog No. K1802-1) with PCR primer P1, revealed similarity to the putative Mlo protein from Arabidopsis thaliana (NCBI gi Accession No. 2459447). These three Arabidopsis thaliana sequences have been identified as Mlo homologs based on sequence comparisons with the Hordeum vulgare Mlo sequence. The BLASTX search using the nucleotide sequences from the contig assembled with the sequence of the entire cDNA in clone cen3n.pk0062.b7 and the sequence of its 5' RACE product obtained using Marathon™ cDNA amplification kit (Clontech catalog No. K1802-1) with PCR primer P4 revealed a higher pLog value to the Mlo protein from Hordeum vulgare (NCBI gi Accession No. 1877221) than did the EST sequence. The BLAST results for each of these sequences are shown in Table 4:

TABLE 4

BLAST Results for Clones Encoding Polypeptides Homologous to Mlo Proteins

| Clone | NCBI gi Accession No. | BLAST pLog Score |
|---|---|---|
| cc3.pk0007.g3 | 2765817 | >254 |
| cr1n.pk0154.a3 | 2765817 | 51.40 |
| cs1.pk0071.e3 | 2765817 | 22.70 |
| cco1.pk0052.b10 | 2252632 | 117.00 |
| cta1.pk0005.c1 + | 2459447 | 177.00 |

TABLE 4-continued

| BLAST Results for Clones Encoding Polypeptides Homologous to Mlo Proteins | | |
|---|---|---|
| Clone | NCBI gi Accession No. | BLAST pLog Score |
| 5' RACE product | | |
| m1o3b3 | 2459447 | 111.00 |
| cen3n.pk0062.b7 + 5' RACE product | 1877221 | 168.00 |

The sequence of the entire cDNA insert in clone cc3.pk0007.g3 was determined and is shown in SEQ ID NO:1; the deduced amino acid sequence of this cDNA is shown in SEQ ID NO:2. The amino acid sequence set forth in SEQ ID NO:2 was evaluated by BLASTP, yielding a pLog value >254 versus the AtMlo-hl protein sequence. The sequence of a portion of the cDNA insert from clone cr1n.pk0154.a3 is shown in SEQ ID NO:3; the deduced amino acid sequence of this cDNA is shown in SEQ ID NO:4. The sequence of a portion of the cDNA insert from clone cs1.pk0071.e3 is shown in SEQ ID NO:5; the deduced amino acid sequence of this cDNA is shown in SEQ ID NO:6. The sequence of the entire cDNA insert in clone cc1.pk0052.b10 was determined and s shown in SEQ ID NO:7; the deduced amino acid sequence of this cDNA is shown in SEQ ID NO:8. The amino acid sequence set forth in SEQ ID NO:8 was evaluated by BLASTP, yielding a pLog value of 97.10 versus the barley Mlo protein isolog from Arabidopsis thaliana. The sequence of the contig assembled with the entire cDNA insert in clone cta1.pk005.c1 and the 5' RACE product obtained using PCR primer P3 is shown in SEQ ID NO:9; the deduced amino acid sequence of this cDNA is shown in SEQ ID NO:10. The amino acid sequence set forth in SEQ ID NO:10 was evaluated by BLASTP, yielding a pLog value of 157.00 versus the putative Mlo protein from Arabidopsis thaliana. The sequence of mlo3b3, the 3' RACE product of cta1.pk0005.c1 obtained using PCR primer P1, is shown in SEQ ID NO:11; the deduced amino acid sequence of this CDNA is shown in SEQ ID NO:12. The sequence of the contig assembled of the CDNA insert from clone cen3n.pk0062.b7 and the 5' RACE product obtained using primer P4 is shown in SEQ ID NO:13; the deduced amino acid sequence of the CDNA is shown in SEQ ID NO:14. Comparison of the 3'-end sequences indicated that clones cs1.pk0071.e3 and cc3.pk0007.g3 are essentially identical at their 3'-untranslated sequences, except for a difference in the polyadenylation site (102 nt insertion), suggesting that these sequences are derived from the same gene. Clones cen3n.pk0062.b7 and cta1.pk0005.c1 differ from each other and from clones cs1.pk0071.e3 and cc3.pk0007.g3 in their 3'-untranslated regions, suggesting that they may be derived from different genes. Clone mlo3b3 has a different 3' end from its parent (cta1.pk0005.c1) suggesting the presence of at least two very similar genes.

The deduced protein sequences were aligned with the NCBI database sequences with the highest pLog and percent similarities were obtained. The data in Table 5 represents a calculation of the percent identity of the amino acid sequences set forth in SEQ ID NOs:2,4,8,10,12 and 14 and the Mlo (or Mlo homolog) sequences present in NCBI.

TABLE 5

| Percent Identity of Amino Acid Sequences Deduced From the Nucleotide Sequences of cDNA Clones Encoding Polypeptides Homologous to Mlo Proteins | | | |
|---|---|---|---|
| Clone | SEQ ID NO. | gi Accession No. | Percent Identity |
| cc3.pk0007.g3 | 2 | 2765817 | 66.4 |
| cr1n.pk0154.a3 | 4 | 2765817 | 65.4 |
| cco1.pk0052.b10 | 8 | 2252632 | 55.4 |
| cta1.pk0005.c1 + 5' RACE product | 10 | 2459447 | 59.2 |
| mlo3b3 | 12 | 2459447 | 60.9 |
| cen3n.pk0062.b7 + 5' RACE product | 14 | 1877221 | 73.7 |

Sequence alignments and percent identity calculations were performed using the Megalign program of the LASAR GENE bioinformatics computing suite (DNASTAR Inc., Madison, Wis.). Sequence percent identity calculations were performed by the Jotun Hein method (Hein, J. J. (1990) Meth. Enz.183:626–645) using the default settings. For multiple alignments gap penalty=11, gap length penalty=3; for pairwise alignments ktuple=2.

Sequence alignments and BLAST scores and probabilities indicate that the instant nucleic acid fragments encode portions, nearly entire, or entire SCLB$^R$ proteins.

Example 4

Characterization of Corn Genomic Fragments Homologous to cDNA clone cta1.pk0005.c1

A pair of PCR primers, P1 and P2, were designed based on the nucleotide sequence of clone cta1.pk0005.c1.

P1 5'-CAGGTTCACCCACGAGACTT-3' (SEQ ID NO:15)

P2 5'-TTGATGAGGAAAGAGCACGA-3' (SEQ ID NO:16)

Genomic DNA was extracted from 12 distinct corn genotypes, including CM37 and T232, and amplified via PCR using primers P1 and P2. Two amplification products were obtained from amplification of CM37 DNA, one of 765 bp in length, and the other of 703 bp in length. In contrast, amplification of T232 genomic DNA yielded a single amplification product of 703 bp in length. Nucleotide sequence analysis of the 765 and 703 bp PCR products (SEQ ID NOs:15 and 16, respectively) revealed a high degree of homology to the nucleotide sequence of the cDNA insert in clone cta1.pk0005.c1. However, sequence analysis revealed that the 703 bp PCR product comprised two introns while the 765 bp product comprised three introns. The nucleotide sequence of the 703 bp PCR product corresponds exactly to the sequence of cta1 .pk0005.c1 cDNA, except for the introns (see FIG. 2). Likewise, the sequence of the 765 bp product is 95% homologous to the cta1.pk0005.c1 insert sequence (again, except for the introns).

Using a 3' RACE amplification system, a cDNA (mlo3b3) was obtained from cta1.pk0005.c1. The nucleotide sequence of mlo3b3 is identical to the 765 bp PCR product without introns (see FIG. 3). Therefore, all three amplification products are related to each other and also to the cta1.pk0005.c1 cDNA insert sequence, and correspond to two corn Mlo-like genes.

Example 5

Genetic Mapping of a Corn Homolog of Barley Mlo

The 765 bp PCR fragment which is produced only from amplification of CM37 genomic DNA and not from T232 genomic DNA is polymorphis between these two genotypes and can therefore be used to map its corresponding gene by analysis of PCR amplification products in a mapping population (48 individuals) resulting from a cross between CM37 and T232. Data was scored on a set of recombinant inbred lines of corn (developed by Dr. Benjamin Burr; see Burr, B. and Burr, F. A. (1991) Trends in Genetics 7:55–60 and Burr, B. et al. (1988) Genetics 118:519–526) from a cross of T232 X CM37. The results of this mapping experiment are shown in Table 6.

TABLE 6

Genotype Data for a Set of Corn Chromosome 6 Markers, Including the cDNA Clone cta1.pk0005.c1

| | Marker Genotype[1,2,3] |
|---|---|
| BNL6.29 | BBBABBBABBBBBBBBAHABBAAABAABHBHBABBABBBABAAAHAABA |
| NP1235 | BBBABBBABBBBBBBABABBAAABAABHBABABBABBBABAAAAAABB |
| BNL7.28 | BBBABBBABBBBBBBABABBAAABAABBBABABBABBBABAAAAAABB |
| ZP15 | ABBABBBABBBBBBBABABBABABAABBBABABBABBBAAAAAAAABB |
| cta1.pk0005.c1 | mmBABBBAABBBBBBABABBABAAmmBBBABABBAmmBBAmAAAAABA |
| MPIK1 | ABBABBBABBBBBBBABABBABAAAABBBABABBABBBAAAAAAABA |
| UMC59 | ABBABBBABBBBBBBABABBABAAAABBBABABBABBBAAAAAAAAA |
| NPI373 | AmBABBBAmBBBHBBABABHABAAAmBmBABABBABBBAAAAmAAAA |
| PIO200045 | mBBABBBABmBmABBABABBABAAHBBBBABABAAABBBAAAAAAAAA |

[1]A designates CM37-like genotype.
[2]B designates T232-like genotype.
[3]Genotypes are listed according to the following order of recombinant inbred lines: 2, 4, 6, 7, 9, 11, 12, 13, 14, 15, 16, 17, 18, 19, 20, 21, 22, 23, 24, 25, 26, 28, 29, 31, 32, 33, 34, 35, 36, 37, 38, 39, 40, 41, 42, 43, 44, 45, 46, 47, 48, 49, 51, 53, 54, 55, 56, 57

The data from this experiment were analyzed using the software program Mapmaker 2.0 for Macintosh (adapted from Mapmaker 2.0 for Unix; Lander et al. (1987) Genomics 1:174–181) in conjunction with segregation data obtained from Dr. Benjamin Burr for a collection of DNA markers scored in that population. The map scores from the public data set were used by Dr. B. Burr to derive map positions and genetic bin assignment, all of which are available in the Maize Genome Database (http://www.agron.missouri.edu). The data presented in Table 6 represents scoring of the RFLP mapping data, except in the case of cta1.pk0005.c1, where the data represents the scoring of the PCR product. The RFLP or PCR pattern was examined and compared to the patterns generated from the parents of the genetic cross which produced the mapping population (i.e., T232 and CM37). If the pattern produced resembled that of CM37, it was designated "A". If the pattern produced resembled that of T232, it was designated "B". If the pattern produced resembled that of both CM37 and T232, it was a heterozygote and thus designated "H". "m" denotes missing data. Mapmaker, when used as described in the instructions accompanying the software, produces a genetic map, which is shown in FIG. 1. This map reveals where the Mlo cDNA clone cta1.pk0005.c1 is positioned with reference to other markers.

The genomic segment corresponding to the 765 bp amplification product was mapped to chromosome 6, in Bin 6.01, defined by markers BNL7.28 and UMC59. Three disease resistance loci map to the same bin on chromosome 6: maize dwarf mosaic virus (MDMV), wheat streak mosaic virus (WSMV) and southern corn leaf blight (SCLB). Of the three disease resistance loci, the SCLB locus is unique in that it is the only known recessive disease resistance locus in corn. Therefore, it is highly likely that the corn Mlo homolog represented by the 765 bp amplification product (containing three introns) corresponds to the southern corn leaf blight resistance gene.

Example 6

Expression of Chimeric Genes in Monocot Cells

A chimeric gene comprising a cDNA encoding a $SCLB^R$ protein in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML 103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML 103. Plasmid pML 103 has been deposited under the terms of the Budapest Treaty at ATCC (American Type Culture Collection, 10801 University Blvd., Manassas, Va. 20110-2209), and bears accession number ATCC 97366. The DNA segment from pML 103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform E. coli XL1-Blue (Epicurian Coli XL-1 Blue™; Stratagene). Bacterial transformanats can be screened by restriction enzyme digestion of plasmid DNA and limited nucleotide sequence analysis using the dideoxy chain termination method (SequenaseT™ DNA Sequencing Kit; U.S. Biochemical). The resulting plasmid construct would comprise a chimeric gene encoding, in the 5' to 3' direction, the maize 27 kD zein promoter, a CDNA fragment encoding a $SCLB^R$ protein, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) Sci. Sin. Peking 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) Nature 313:810–812) and 3' region of the nopaline synthase gene from the T-DNA of the Ti plasmid of Agrobacterium tumefaciens.

The particle bombardment method (Klein et al., (1987) Nature 327:70–73) may be used to transfer genes to the callus culture cells. According to this method, gold particles (1 $\mu$m in diameter) are coated with DNA using the following technique. Ten $\mu$g of plasmid DNAs are added to 50 $\mu$L of a suspension of gold particles (60 mg per mL). Calcium chloride (50 $\mu$L of a 2.5 M Solution) and spermidine free base (20 $\mu$L of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 $\mu$L of absolute ethanol, centrifuged again and the supernatant removed. The ethanol rinse is performed again and the particles resuspended in a final volume of 30 )$\mu$L of ethanol. An aliquot (5 $\mu$L) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that burst when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of active growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) Bio/Technology 8:833–839).

Example 7

Expression of Chimeric Genes in Dicot Cells

A seed-specific expression cassette composed of the promoter and transcription terminator from the gene encoding the P subunit of the seed storage protein phaseolin from the bean Phaseolus vulgaris (Doyle et al. (1986) J. Biol. Chem.261:9228–923 8) can be used for expression of the instant $SCLB^R$ proteins in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is than performed as described above, and the isolated fragment is inserted into a pUC 18 vector carrying the seed expression cassette.

Soybean embroys may then be transformed with the expression vector comprising sequences encoding $SCLB^R$ proteins. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Kline et al. (1987) Nature (London) 327:70, U.S. Pat. No. 4,945,050). A Du Pont Biolistic™ PDS1000/HE instrument (helium retrofit) can be used for these transformations.

A selectable marker gene which can be used to facilitate soybean transformation is a chimeric gene composed of the 35S promoter from cauliflower mosaic virus (Odell et al. (1985) Nature 313:810–812), the hygromycin phosphotransferase gene from plasmid pJR225 (from E. coli; Gritz et al. (1983) Gene 25:179–188) and the 3' region of the nopaline synthase gene from the T-DNA of the Ti plasmid of Agrobacterium tumefaciens. The seed expression cassette comprising the phaseolin 5' region, the fragment encoding the $SCLB^R$ protein and the phaseolin 3' region can be isolated as a restriction fragment. This fragment can then be inserted into a unique restriction site of the vector carrying the marker gene. To 50 $\mu$L of a 60 mg/mL 1 $\mu$m gold particle suspension is added (in order):5 $\mu$L DNA (1 $\mu$g/$\mu$L), 20 $\mu$L spermidine (0.1 M), and 50 $\mu$L $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk. Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germinations of individual somatic embryos.

Example 8

Expression of Chimeric Genes in Microbial Cells

The cDNAs encoding the instant corn $SCLB^R$ proteins can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using Oligonucleotide-directed mutagenesis. The DNA sequence of pET-3aM in this region, 5'-CATATGG, was converted to 5'-CCCATGG in pBT430.

Plasmid DNA containing a CDNA may be appropriately digested to release a nucleic acid fragment encoding the protein. This fragment may then be purified on a 1% NuSieve GTG™ low melting agarose gel (FMC). Buffer and a(garose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkalinephosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the $SCLB^R$ protein are then screened for the correct orientation with respect to the T7 promoter by restriction enzyme analysis.

For high level expression, a plasmid clone with the cDNA insert in the correct orientation relative to the T7 promoter can be transformed into E. coli strain BL21 (DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One lig of protein from the soluble fraction of the culture can be separated by SDS-polyacrylamide gel electrophoresis. Gels can be observed for protein bands migrating at the expected molecular weight.

SEQUENCE LISTING

```
<160> NUMBER OF SEQ ID NOS: 20

<210> SEQ ID NO 1
<211> LENGTH: 1725
<212> TYPE: DNA
<213> ORGANISM: Zea mays

<400> SEQUENCE: 1

gcacgagggc cgagggcgag gcggcggcgc tggagttcac accgacgtgg atcgtcgcgg      60

cggtctgctc tctcatcgtg ctcctctcgc tcgtcgccga gcgatgcctc cactacctcg     120

gcaagacgct caagaggaag aaccagaagc cgctcttcga ggcgctgctc aaggtcaaag     180

aagagttgat gcttctgggg ttcatctccc tgctgctgac ggtgttccag gggatgatcc     240

ggaggacgtg catccctgaa cgctggacat tccacatgct gccatgcgag aagccagatg     300
```

-continued

```
agaaggccgg tgaggccgcc accatggagc attttgtagg gacgcttggc aggatcggta    360

ggcgtctgtt gcaggaaggc actgctgggg ctgagcaatg ccagaagaag ggaaaagttc    420

cacttttgtc ccttgaagcc atacatcagc tgcacatttt catatttgtt ctggcaatca    480

cacatgttat tttcagcgtc acaactatgc ttttaggagg tgcacagata caccaatgga    540

aacagtggga gaatggaatt aaaaaagatg ctcctggaaa tgggcctaag gtaaccaatg    600

tacatcatca tgaatttatc aagaaacgtt ttaagggtat tggcaaagat tctataatat    660

tgagttggct gcattctttt ggtaagcagt tttatagatc agtatctaaa tcagattaca    720

ccacaatgcg tcttggtttt atcatgactc actgccctgg aaatccaaaa tttgatttcc    780

atagatacat ggtaagggtt ttagaggcgg attttaagaa agtggtaggc ataagctggt    840

acttgtgggt cttcgtggtg atatttctgt tgctgaatgt taatggctgg cacacatact    900

tttggattgc tttccttccc cttattcttc tgttagccat tggcactaag ctggagcatg    960

tcatagctca gctagcccat gatgtagctg agaagcacac agcggtcgag ggcgatgtga   1020

tcgtaaaacc atcagatgaa cacttctggt tcggcaagcc tagggttatc ctttacctga   1080

tccacttcat cctctttcag aatgcgtttg agattgcgtt tttcttctgg atactgagca   1140

cttatggatt cgactcgtgc atcatgggac aagttcgttt tattgtgcca aggcttgtca   1200

tcggggtggt tattcagctt ctctgcagct acagcacctt gcctctgtat gcaattgtaa   1260

cccagatggg gagctgctac aagaaggaga tcttcaacga gcatgtgcag cagggcgtcc   1320

tgggctgggc tcagaaggtc aagatgaaaa agggactgaa gggagctgca tctgctagca   1380

aggacgaatc gattaccaat gccgattcgg caggaccttc cgttaagatt gaaatggcga   1440

aggctgggga ggatgttgag atcgttggaa acacaggttg attgggacaa tagggtgccc   1500

gtgttgtaat gatgtaacag gttaatatgc catcatcttt ttttgtagat actagatagc   1560

ttgctgtggc aataccgcaa tagcggtgaa ctagagaagg tgagtttggg cccgggagcc   1620

tcatctgtta tcggtccagt aggaagcaaa ttcttatata cgggatatcg ataagaaatg   1680

aactaagaac atgttcctgg attaaaaaaa aaaaaaaaaa aaaaa                   1725
```

<210> SEQ ID NO 2
<211> LENGTH: 492
<212> TYPE: PRT
<213> ORGANISM: Zea mays

<400> SEQUENCE: 2

```
Thr Arg Ala Glu Gly Glu Ala Ala Ala Leu Glu Phe Thr Pro Thr Trp
  1               5                  10                  15

Ile Val Ala Ala Val Cys Ser Leu Ile Val Leu Leu Ser Leu Val Ala
             20                  25                  30

Glu Arg Cys Leu His Tyr Leu Gly Lys Thr Leu Lys Arg Lys Asn Gln
         35                  40                  45

Lys Pro Leu Phe Glu Ala Leu Leu Lys Val Lys Glu Glu Leu Met Leu
     50                  55                  60

Leu Gly Phe Ile Ser Leu Leu Leu Thr Val Phe Gln Gly Met Ile Arg
 65                  70                  75                  80

Arg Thr Cys Ile Pro Glu Arg Trp Thr Phe His Met Leu Pro Cys Glu
                 85                  90                  95

Lys Pro Asp Glu Lys Ala Gly Glu Ala Ala Thr Met Glu His Phe Val
            100                 105                 110

Gly Thr Leu Gly Arg Ile Gly Arg Arg Leu Leu Gln Glu Gly Thr Ala
        115                 120                 125
```

-continued

```
Gly Ala Glu Gln Cys Gln Lys Lys Gly Lys Val Pro Leu Leu Ser Leu
    130                 135                 140

Glu Ala Ile His Gln Leu His Ile Phe Ile Phe Val Leu Ala Ile Thr
145                 150                 155                 160

His Val Ile Phe Ser Val Thr Thr Met Leu Leu Gly Gly Ala Gln Ile
                165                 170                 175

His Gln Trp Lys Gln Trp Glu Asn Gly Ile Lys Lys Asp Ala Pro Gly
            180                 185                 190

Asn Gly Pro Lys Val Thr Asn Val His His His Glu Phe Ile Lys Lys
        195                 200                 205

Arg Phe Lys Gly Ile Gly Lys Asp Ser Ile Ile Leu Ser Trp Leu His
    210                 215                 220

Ser Phe Gly Lys Gln Phe Tyr Arg Ser Val Ser Lys Ser Asp Tyr Thr
225                 230                 235                 240

Thr Met Arg Leu Gly Phe Ile Met Thr His Cys Pro Gly Asn Pro Lys
                245                 250                 255

Phe Asp Phe His Arg Tyr Met Val Arg Val Leu Glu Ala Asp Phe Lys
            260                 265                 270

Lys Val Val Gly Ile Ser Trp Tyr Leu Trp Val Phe Val Val Ile Phe
        275                 280                 285

Leu Leu Leu Asn Val Asn Gly Trp His Thr Tyr Phe Trp Ile Ala Phe
    290                 295                 300

Leu Pro Leu Ile Leu Leu Leu Ala Ile Gly Thr Lys Leu Glu His Val
305                 310                 315                 320

Ile Ala Gln Leu Ala His Asp Val Ala Glu Lys His Thr Ala Val Glu
                325                 330                 335

Gly Asp Val Ile Val Lys Pro Ser Asp Glu His Phe Trp Phe Gly Lys
            340                 345                 350

Pro Arg Val Ile Leu Tyr Leu Ile His Phe Ile Leu Phe Gln Asn Ala
        355                 360                 365

Phe Glu Ile Ala Phe Phe Phe Trp Ile Leu Ser Thr Tyr Gly Phe Asp
    370                 375                 380

Ser Cys Ile Met Gly Gln Val Arg Phe Ile Val Pro Arg Leu Val Ile
385                 390                 395                 400

Gly Val Val Ile Gln Leu Leu Cys Ser Tyr Ser Thr Leu Pro Leu Tyr
                405                 410                 415

Ala Ile Val Thr Gln Met Gly Ser Cys Tyr Lys Lys Glu Ile Phe Asn
            420                 425                 430

Glu His Val Gln Gln Gly Val Leu Gly Trp Ala Gln Lys Val Lys Met
        435                 440                 445

Lys Lys Gly Leu Lys Gly Ala Ala Ser Ala Ser Lys Asp Glu Ser Ile
    450                 455                 460

Thr Asn Ala Asp Ser Ala Gly Pro Ser Val Lys Ile Glu Met Ala Lys
465                 470                 475                 480

Ala Gly Glu Asp Val Glu Ile Val Gly Asn Thr Gly
                485                 490
```

<210> SEQ ID NO 3
<211> LENGTH: 597
<212> TYPE: DNA
<213> ORGANISM: Zea mays
<220> FEATURE:
<221> NAME/KEY: unsure
<222> LOCATION: (3)
<220> FEATURE:

-continued

<221> NAME/KEY: unsure
<222> LOCATION: (475)
<220> FEATURE:
<221> NAME/KEY: unsure
<222> LOCATION: (520)
<220> FEATURE:
<221> NAME/KEY: unsure
<222> LOCATION: (538)
<220> FEATURE:
<221> NAME/KEY: unsure
<222> LOCATION: (540)
<220> FEATURE:
<221> NAME/KEY: unsure
<222> LOCATION: (552)
<220> FEATURE:
<221> NAME/KEY: unsure
<222> LOCATION: (559)
<220> FEATURE:
<221> NAME/KEY: unsure
<222> LOCATION: (568)
<220> FEATURE:
<221> NAME/KEY: unsure
<222> LOCATION: (571)
<220> FEATURE:
<221> NAME/KEY: unsure
<222> LOCATION: (583)

<400> SEQUENCE: 3 crnkagtgga acactatccc gagaaaccag atattgattt ccacaaatac atgactcgcg 60 ctgttgaata tgagtttaaa agagttgttg gtatcagctg gtatctgtgg ctttttgtaa 120 tcttattcct gctgctgaat ataaatggat ggcacacata cttctggttg gctttcttgc 180 ctctatttct gttacttatt gttggtgcca aactagagca cattatcact cggttggctc 240 aagaggcagc gatatcatta tcaaataata cagaggaagt tccgaaaata aagccatgca 300 aggaccattt ctggtttcac aagcctgagc tagtccttca tttgattcat ttcatcctgt 360 tccagaattc gttcgagatt agtttttcc tcctggattc tggtatcaga aggtttcggt 420 tcgtgtatga tggaacggaa gcttatgtca tttccagact tgttatcggg tgatnatcga 480 agtcacctgc agctatatca cccgccacta tacgcaacgn gaccaatatg accggcangn 540 taagctgatg gntttggcnc cgcgtgcnca natgtcaagg gcnggtttgg tttagga 597

<210> SEQ ID NO 4
<211> LENGTH: 80
<212> TYPE: PRT
<213> ORGANISM: Zea mays

<400> SEQUENCE: 4

His Tyr Pro Glu Lys Pro Asp Ile Asp Phe His Lys Tyr Met Thr Arg
1 5 10 15

Ala Val Glu Tyr Glu Phe Lys Arg Val Val Gly Ile Ser Trp Tyr Leu
20 25 30

Trp Leu Phe Val Ile Leu Phe Leu Leu Leu Asn Ile Asn Gly Trp His
35 40 45

Thr Tyr Phe Trp Leu Ala Phe Leu Pro Leu Phe Leu Leu Leu Ile Val
50 55 60

Gly Ala Lys Leu Glu His Ile Ile Thr Arg Leu Ala Gln Glu Ala Ala
65 70 75 80

<210> SEQ ID NO 5
<211> LENGTH: 472
<212> TYPE: DNA
<213> ORGANISM: Zea mays
<220> FEATURE:
<221> NAME/KEY: unsure -continued <222> LOCATION: (164)
<220> FEATURE:
<221> NAME/KEY: unsure
<222> LOCATION: (351)
<220> FEATURE:
<221> NAME/KEY: unsure
<222> LOCATION: (379)
<220> FEATURE:
<221> NAME/KEY: unsure
<222> LOCATION: (398)
<220> FEATURE:
<221> NAME/KEY: unsure
<222> LOCATION: (414)
<220> FEATURE:
<221> NAME/KEY: unsure
<222> LOCATION: (427)
<220> FEATURE:
<221> NAME/KEY: unsure
<222> LOCATION: (439)..(440)
<220> FEATURE:
<221> NAME/KEY: unsure
<222> LOCATION: (447)
<220> FEATURE:
<221> NAME/KEY: unsure
<222> LOCATION: (450)

<400> SEQUENCE: 5 gtgcatcatg ggacaagttc gttttattgt gccaaggctt gtcatcgggt atttaaatcg 60 ttgaaaacac atccatttca tgaggaaaag aaaaaaaaac atcaatatgt tatgttctct 120 tgacactagt atccacgctt tgtacttgca gggtggttat tcancttctc tgcagctaca 180 gcaccttgcc tctgtatgca attgtaaccc agatggggag ctgctacaag aaggagatct 240 tcaacgagca tgtgcagcag ggcgtcctgg gctgggctca gaaggtcaag atgaaaaagg 300 gactgaggga gctgcatctg ctagcaagga cgaatcgtta ccaatgccga ntcggcagga 360 ccttccgtta agattgaang gcgaagctgg ggaggatntt gagaccttgg aaanaggatg 420 attgganaaa aggtcccgnn tgaaatnagn acagttatat caacacttta aa 472

<210> SEQ ID NO 6
<211> LENGTH: 52
<212> TYPE: PRT
<213> ORGANISM: Zea mays
<220> FEATURE:
<221> NAME/KEY: UNSURE
<222> LOCATION: (4)

<400> SEQUENCE: 6

Val Val Ile Xaa Leu Leu Cys Ser Tyr Ser Thr Leu Pro Leu Tyr Ala
1 5 10 15

Ile Val Thr Gln Met Gly Ser Cys Tyr Lys Lys Glu Ile Phe Asn Glu
20 25 30

His Val Gln Gln Gly Val Leu Gly Trp Ala Gln Lys Val Lys Met Lys
35 40 45

Lys Gly Leu Arg
50

<210> SEQ ID NO 7
<211> LENGTH: 1831
<212> TYPE: DNA
<213> ORGANISM: Zea mays

<400> SEQUENCE: 7 ccagatatca gggcagctgg aactgaaggt ggcgggagcc gagtgatccg gcggtgagct 60 gagcggggcg ggatggcggc ggagcagggg cggtcgctgg cggagacgcc cacctggtcc 120

-continued

```
gtggcaaccg tcaccacgct catggtcgct gcctgcttcc tcgtcgagcg ctccctctcg    180

cgcttcgcca agtggctgcg caagaccaag cggaaggcca tgctcgccgc gctcgagaag    240

atccgcgaag agctgatgct gctcggagtc atctcgctgc tgctcagcca gacggcgcgc    300

ttcatatcgg agatctgcgt gccgtcctcg ctcttcacca gccgcttcta catctgctcc    360

gagagcgact accaggacct gctgcgcaac acggacgcca accagacggc gctcgacaag    420

aacatgttcg gtggccaacg gctgcacgtc tgtggcgagg gccatgaacc ttttgtttcg    480

tacgagggcc ttgagcagct gcaccggttt ctcttcatcc ttggtatcac tcatgtgttg    540

tacagttttg taacagtggt tctgtccatg atcaagatct atagctggag gaagtgggaa    600

accttagcag gtccaattgc tgctgaggaa ttgaaagcta ggagaaccaa ggtgatgaga    660

aggcagtcaa cctttgtttt taacaatgct tctcatccat ggagcaaaaa taaaatactt    720

atttggatgc tttgcttttt gcgtcaattc aagggctcca taataaggtc agactatttg    780

gcactgaggt tgggctttgt cacatatcac aagctaccac attcatatga cttccataaa    840

tacatggtac ggagcatgga agatgattac aatgggacta ttggtatcag ttggccactt    900

tgggcatatg cgattgtctg catattaatc aatgttcatg gtatcaatat atatttctgg    960

ttgtcctttg ttcctgttat tctggtgctt ctagtgggta ctgaacttca gcacgtcatt   1020

gctcagttgg ctttggaagt cgctgaggca acagcgcctt atgttggctc acaacttaaa   1080

ctgcgtgatg atctattttg gtttggaaag cctcgggtac tctggtggct tatacagttc   1140

atttcatttc agaatgcttt tgagctggca acattcttat ggtctctgtg ggaactcagt   1200

gcacaaacat gtttcatgaa gcactactac atggttgcca ttcggttgat ttctgggctc   1260

ttagttcagt tttggtgcag ctacagcaca ctcccgctga atgtgattat ttctcagatg   1320

ggtcccaagt tcaagaaatc actggtctcg gagaacgtga gggagtcgct gcacagctgg   1380

tgcaagaggg ttaaggacag gagccgacac aatccgctct tctcgcggaa cgggaccctc   1440

acgaccagat ccgtgtgctc cctagacacc acctacgaga cggatcacga gacgaacacg   1500

gtgtgcacgc tgtcgaggac ggcgtcggcg acgtcgctgg acgaccagtt gaccgtggtc   1560

accgtcgatg acgagccgtc ctgcattgag aaggatgtct gacgcagttg ctgattcgcc   1620

aaaactacat actgcaccga cctgtgtgtt aggaggtact ctaggactga aattgttcac   1680

ggcgtggcgc gctctgaact agtaatgtcg ccgcggagag tgcttgaccc gcgctacgtg   1740

ggagaggcat aactattgta gtgaggtaaa ttggggaggg ggtagatgaa gagtcgccgg   1800

tggatggtgt gttgcacggc aagagacgac a                                  1831
```

<210> SEQ ID NO 8
<211> LENGTH: 509
<212> TYPE: PRT
<213> ORGANISM: Zea mays

<400> SEQUENCE: 8

```
Met Ala Ala Glu Gln Gly Arg Ser Leu Ala Glu Thr Pro Thr Trp Ser
  1               5                  10                  15

Val Ala Thr Val Thr Thr Leu Met Val Ala Ala Cys Phe Leu Val Glu
             20                  25                  30

Arg Ser Leu Ser Arg Phe Ala Lys Trp Leu Arg Lys Thr Lys Arg Lys
         35                  40                  45

Ala Met Leu Ala Ala Leu Glu Lys Ile Arg Glu Glu Leu Met Leu Leu
     50                  55                  60

Gly Val Ile Ser Leu Leu Leu Ser Gln Thr Ala Arg Phe Ile Ser Glu
```

-continued

```
 65                  70                  75                  80

Ile Cys Val Pro Ser Ser Leu Phe Thr Ser Arg Phe Tyr Ile Cys Ser
                85                  90                  95

Glu Ser Asp Tyr Gln Asp Leu Leu Arg Asn Thr Asp Ala Asn Gln Thr
            100                 105                 110

Ala Leu Asp Lys Asn Met Phe Gly Gly Gln Arg Leu His Val Cys Gly
        115                 120                 125

Glu Gly His Glu Pro Phe Val Ser Tyr Glu Gly Leu Glu Gln Leu His
    130                 135                 140

Arg Phe Leu Phe Ile Leu Gly Ile Thr His Val Leu Tyr Ser Phe Val
145                 150                 155                 160

Thr Val Val Leu Ser Met Ile Lys Ile Tyr Ser Trp Arg Lys Trp Glu
                165                 170                 175

Thr Leu Ala Gly Pro Ile Ala Ala Glu Glu Leu Lys Ala Arg Arg Thr
            180                 185                 190

Lys Val Met Arg Arg Gln Ser Thr Phe Val Phe Asn Asn Ala Ser His
        195                 200                 205

Pro Trp Ser Lys Asn Lys Ile Leu Ile Trp Met Leu Cys Phe Leu Arg
    210                 215                 220

Gln Phe Lys Gly Ser Ile Ile Arg Ser Asp Tyr Leu Ala Leu Arg Leu
225                 230                 235                 240

Gly Phe Val Thr Tyr His Lys Leu Pro His Ser Tyr Asp Phe His Lys
                245                 250                 255

Tyr Met Val Arg Ser Met Glu Asp Asp Tyr Asn Gly Thr Ile Gly Ile
            260                 265                 270

Ser Trp Pro Leu Trp Ala Tyr Ala Ile Val Cys Ile Leu Ile Asn Val
        275                 280                 285

His Gly Ile Asn Ile Tyr Phe Trp Leu Ser Phe Val Pro Val Ile Leu
    290                 295                 300

Val Leu Leu Val Gly Thr Glu Leu Gln His Val Ile Ala Gln Leu Ala
305                 310                 315                 320

Leu Glu Val Ala Glu Ala Thr Ala Pro Tyr Val Gly Ser Gln Leu Lys
                325                 330                 335

Leu Arg Asp Asp Leu Phe Trp Phe Gly Lys Pro Arg Val Leu Trp Trp
            340                 345                 350

Leu Ile Gln Phe Ile Ser Phe Gln Asn Ala Phe Glu Leu Ala Thr Phe
        355                 360                 365

Leu Trp Ser Leu Trp Glu Leu Ser Ala Gln Thr Cys Phe Met Lys His
    370                 375                 380

Tyr Tyr Met Val Ala Ile Arg Leu Ile Ser Gly Leu Leu Val Gln Phe
385                 390                 395                 400

Trp Cys Ser Tyr Ser Thr Leu Pro Leu Asn Val Ile Ile Ser Gln Met
                405                 410                 415

Gly Pro Lys Phe Lys Lys Ser Leu Val Ser Glu Asn Val Arg Glu Ser
            420                 425                 430

Leu His Ser Trp Cys Lys Arg Val Lys Asp Arg Ser Arg His Asn Pro
        435                 440                 445

Leu Phe Ser Arg Asn Gly Thr Leu Thr Thr Arg Ser Val Cys Ser Leu
    450                 455                 460

Asp Thr Thr Tyr Glu Thr Asp His Glu Thr Asn Thr Val Cys Thr Leu
465                 470                 475                 480

Ser Arg Thr Ala Ser Ala Thr Ser Leu Asp Asp Gln Leu Thr Val Val
                485                 490                 495
```

-continued

```
Thr Val Asp Asp Glu Pro Ser Cys Ile Glu Lys Asp Val
            500                 505


<210> SEQ ID NO 9
<211> LENGTH: 1851
<212> TYPE: DNA
<213> ORGANISM: Zea mays

<400> SEQUENCE: 9

cccggtgatc gtatcgtcga ttggaagtga agatcaagcg atcgatagaa taaattaaag     60

gcgcgggggc aacaacaaga atgggggcg gtggcggtgg cggcaactcg cgggagcttg    120

accagacgcc gacatgggcg gtggcgtcgg tgtgcggcgt gatcgtgctc atctccatcc    180

tgctggagaa ggggctccac cacgtgggcg agttcttctc ccaccgcaag aagaaggcca    240

tggtggaggc cctggagaag gtgaaggcgg agctcatggt gctgggcttc atctcgctcc    300

tcctcgtgtt cggccagaac tacatcatca aggtctgcat cagcaaccac gccgccaaca    360

ccatgctccc ctgcaagctc gaggccgccg ccgtcgaggg caaggacggc cacggcaagg    420

aggccgccgc cgtggtcgct ggcaagaaga aggtcgccgt cgccgtccct ggaaagaaga    480

agaagaaggc cgccgccgcc gccgaccatc ttggcggtgt ggtggactgg ccgccgccct    540

actacgcgca caacgccagg atgctggcgg aggcgagcat ggcgaccaag tgccccgagg    600

ggaaagtgcc gctcatctcc atcaacgccc tgcaccagct gcacatcttc atcttcttcc    660

tcgccgtctt ccacgtctcc tacagcgcaa tcaccatggc gctcggcagg gccaagatac    720

gtgcatggaa agagtgggag aaagaagctg caggacaaga ctacgagttc tcacatgacc    780

cgacgcggtt caggttcacc cacgagactt ccttcgtgag gcagcatatg aatgtgctga    840

acaagttccc agcatcattc tacatcagca acttcttccg gcagttcttc aggtccgtga    900

ggcaggcaga ctactgcgcg ctgcgccaca gctttgtcaa cgtccatctg gcccctggca    960

gcaagtttga tttccagaag tacatcaagc ggtctctgga ggatgacttc aaggtgatcg   1020

tggggatcag tcctcctctg tgggcttctg ctctcatctt cctcttcctc aacgtcaatg   1080

gatggcacac catgctctgg atctccatca tgccggtggt gatcatcctg tcggtgggga   1140

cgaagctgca gggcatcatc tgccgcatgg cgatcgacat cacggagcgc cacgccgtca   1200

tccagggcat cccgatggtg caagtcagcg actcctactt ctggttcgca cgccccacct   1260

tcgtgctctt cctcatccac ttcaccctct tccagaatgg cttccagatc atctacttcc   1320

tctggattct gtatgagtac ggcatggact cgtgcttcaa cgactccgaa gagttcgtct   1380

ttgcacgact ctgccttggc gtggttgtcc aggtgctgtg cagctacgtg acgctcccgc   1440

tgtacgcgct cgtctcccaa atgggctcca ccatgaagca gtccatcttc gacgagcaga   1500

cctccaaggc gctcaagaac tggcgcgccg gcgccaagaa gaaggctccc accggcggct   1560

ccaagcacgg cggtggtggc tcccccaccg ccggcggcag ccccaccaag gccgacggcg   1620

acgcgtagag aggaacacgc taactttaat ttctgtgtgc ttaattgcct aggctcgtta   1680

agtcagaaca tgcatgcatg taacaccact gctggttttc atatagtgtc gacagatggt   1740

caacgtactt tttgcgatcc cacttgtatt tttttttac aatgaagcac ccgtccgcgt   1800

ccgtggacac tgcaagtgca aaaaaaaaaa aaaaaaaaaa aaaaaaaaaa a           1851


<210> SEQ ID NO 10
<211> LENGTH: 515
<212> TYPE: PRT
<213> ORGANISM: Zea mays
```

-continued

<400> SEQUENCE: 10

Met Gly Gly Gly Gly Gly Gly Gly Asn Ser Arg Glu Leu Asp Gln Thr
1 5 10 15

Pro Thr Trp Ala Val Ala Ser Val Cys Gly Val Ile Val Leu Ile Ser
20 25 30

Ile Leu Leu Glu Lys Gly Leu His His Val Gly Glu Phe Phe Ser His
35 40 45

Arg Lys Lys Lys Ala Met Val Glu Ala Leu Glu Lys Val Lys Ala Glu
50 55 60

Leu Met Val Leu Gly Phe Ile Ser Leu Leu Leu Val Phe Gly Gln Asn
65 70 75 80

Tyr Ile Ile Lys Val Cys Ile Ser Asn His Ala Ala Asn Thr Met Leu
85 90 95

Pro Cys Lys Leu Glu Ala Ala Ala Val Glu Gly Lys Asp Gly His Gly
100 105 110

Lys Glu Ala Ala Ala Val Val Ala Gly Lys Lys Lys Val Ala Val Ala
115 120 125

Val Pro Gly Lys Lys Lys Lys Lys Ala Ala Ala Ala Ala Asp His Leu
130 135 140

Gly Gly Val Val Asp Trp Pro Pro Pro Tyr Tyr Ala His Asn Ala Arg
145 150 155 160

Met Leu Ala Glu Ala Ser Met Ala Thr Lys Cys Pro Glu Gly Lys Val
165 170 175

Pro Leu Ile Ser Ile Asn Ala Leu His Gln Leu His Ile Phe Ile Phe
180 185 190

Phe Leu Ala Val Phe His Val Ser Tyr Ser Ala Ile Thr Met Ala Leu
195 200 205

Gly Arg Ala Lys Ile Arg Ala Trp Lys Glu Trp Glu Lys Glu Ala Ala
210 215 220

Gly Gln Asp Tyr Glu Phe Ser His Asp Pro Thr Arg Phe Arg Phe Thr
225 230 235 240

His Glu Thr Ser Phe Val Arg Gln His Met Asn Val Leu Asn Lys Phe
245 250 255

Pro Ala Ser Phe Tyr Ile Ser Asn Phe Phe Arg Gln Phe Phe Arg Ser
260 265 270

Val Arg Gln Ala Asp Tyr Cys Ala Leu Arg His Ser Phe Val Asn Val
275 280 285

His Leu Ala Pro Gly Ser Lys Phe Asp Phe Gln Lys Tyr Ile Lys Arg
290 295 300

Ser Leu Glu Asp Asp Phe Lys Val Ile Val Gly Ile Ser Pro Pro Leu
305 310 315 320

Trp Ala Ser Ala Leu Ile Phe Leu Phe Leu Asn Val Asn Gly Trp His
325 330 335

Thr Met Leu Trp Ile Ser Ile Met Pro Val Val Ile Ile Leu Ser Val
340 345 350

Gly Thr Lys Leu Gln Gly Ile Ile Cys Arg Met Ala Ile Asp Ile Thr
355 360 365

Glu Arg His Ala Val Ile Gln Gly Ile Pro Met Val Gln Val Ser Asp
370 375 380

Ser Tyr Phe Trp Phe Ala Arg Pro Thr Phe Val Leu Phe Leu Ile His
385 390 395 400

Phe Thr Leu Phe Gln Asn Gly Phe Gln Ile Ile Tyr Phe Leu Trp Ile

-continued

```
                405                 410                 415

Leu Tyr Glu Tyr Gly Met Asp Ser Cys Phe Asn Asp Ser Glu Glu Phe
            420                 425                 430

Val Phe Ala Arg Leu Cys Leu Gly Val Val Val Gln Val Leu Cys Ser
        435                 440                 445

Tyr Val Thr Leu Pro Leu Tyr Ala Leu Val Ser Gln Met Gly Ser Thr
    450                 455                 460

Met Lys Gln Ser Ile Phe Asp Glu Gln Thr Ser Lys Ala Leu Lys Asn
465                 470                 475                 480
Trp Arg Ala Gly Ala Lys Lys Lys Ala Pro Thr Gly Gly Ser Lys His
                485                 490                 495

Gly Gly Gly Gly Ser Pro Thr Ala Gly Gly Ser Pro Thr Lys Ala Asp
            500                 505                 510

Gly Asp Ala
        515


<210> SEQ ID NO 11
<211> LENGTH: 1040
<212> TYPE: DNA
<213> ORGANISM: Zea mays

<400> SEQUENCE: 11

aggttcaccc acgagacttc gtttgtgagg cagcatatga atgtgctcaa caagttccca     60

gcatccttct acatcagcaa cttcttccgg cagttcttca ggtccgtcag gcgggcagac    120

tactgcgcgc tgcgccacag ctttgtcaac gtccatctgg cccctggcac caagtttgat    180

ttccaaaagt acatcaagcg gtctctggag gacgacttca aggtgatcgt ggggatcagc    240

cctcctttgt gggcttctgc tctcatcttc ctattcctca atgtcaatgg atggcacacc    300

atgctctgga tctccatcat gccggtggtg atcatcctgt ccgtggggac gaagctgcag    360

ggcatcatct gccgcatggc gatcgacatc acggagcggc acgccgtgat ccagggcatc    420

ccgctggtgc aggtcagcga ctcctacttc tggttcgcac gcccaacctt cgtgctcttc    480

ctcatccact tcaccctctt ccagaatggc ttccagatca tctacttcct ctggattctg    540

tatgagtacg ggatggactc gtgcttcaac gactccgaag aattcgtctt tgcacgtctc    600

tgccttgggg tggttgttca ggtgctgtgc agctacgtga cgctccctct gtacgcgctc    660

gtctcccaga tgggctccac catgaagcag tccatcttcg acgagcagac ctccaaggcg    720

ctcaagaact ggcgcgccgg cgccaagaag aaggccccca ccggcagccc caccaaggcc    780

gacggcgacg cgtagacgta gctagcagag ggtcatcgat cgattgatcg atcgatccag    840

ctgttcgttc tacatataac ctgttactta tttgtatgta attgtaccaa tagcaatcga    900

cacgcgtgcg ccgcatgcaa tgtaccatga aactgctgat agctagagag cgacattttt    960

cttgtttggt tcgtttctgc aatgctccta ctatgtaatt gtcagttatc caaaaaaaaa   1020

aaaaaaaaaa aaaaaaaaaa                                               1040


<210> SEQ ID NO 12
<211> LENGTH: 264
<212> TYPE: PRT
<213> ORGANISM: Zea mays

<400> SEQUENCE: 12

Arg Phe Thr His Glu Thr Ser Phe Val Arg Gln His Met Asn Val Leu
  1               5                  10                  15

Asn Lys Phe Pro Ala Ser Phe Tyr Ile Ser Asn Phe Phe Arg Gln Phe
            20                  25                  30
```

-continued

```
Phe Arg Ser Val Arg Arg Ala Asp Tyr Cys Ala Leu Arg His Ser Phe
         35                  40                  45

Val Asn Val His Leu Ala Pro Gly Thr Lys Phe Asp Phe Gln Lys Tyr
     50                  55                  60

Ile Lys Arg Ser Leu Glu Asp Asp Phe Lys Val Ile Val Gly Ile Ser
 65                  70                  75                  80

Pro Pro Leu Trp Ala Ser Ala Leu Ile Phe Leu Phe Leu Asn Val Asn
                 85                  90                  95

Gly Trp His Thr Met Leu Trp Ile Ser Ile Met Pro Val Val Ile Ile
            100                 105                 110

Leu Ser Val Gly Thr Lys Leu Gln Gly Ile Ile Cys Arg Met Ala Ile
        115                 120                 125

Asp Ile Thr Glu Arg His Ala Val Ile Gln Gly Ile Pro Leu Val Gln
    130                 135                 140

Val Ser Asp Ser Tyr Phe Trp Phe Ala Arg Pro Thr Phe Val Leu Phe
145                 150                 155                 160

Leu Ile His Phe Thr Leu Phe Gln Asn Gly Phe Gln Ile Ile Tyr Phe
                165                 170                 175

Leu Trp Ile Leu Tyr Glu Tyr Gly Met Asp Ser Cys Phe Asn Asp Ser
            180                 185                 190

Glu Glu Phe Val Phe Ala Arg Leu Cys Leu Gly Val Val Val Gln Val
        195                 200                 205

Leu Cys Ser Tyr Val Thr Leu Pro Leu Tyr Ala Leu Val Ser Gln Met
    210                 215                 220

Gly Ser Thr Met Lys Gln Ser Ile Phe Asp Glu Gln Thr Ser Lys Ala
225                 230                 235                 240

Leu Lys Asn Trp Arg Ala Gly Ala Lys Lys Lys Ala Pro Thr Gly Ser
                245                 250                 255

Pro Thr Lys Ala Asp Gly Asp Ala
            260


<210> SEQ ID NO 13
<211> LENGTH: 538
<212> TYPE: DNA
<213> ORGANISM: Zea mays
<220> FEATURE:
<221> NAME/KEY: unsure
<222> LOCATION: (479)
<220> FEATURE:
<221> NAME/KEY: unsure
<222> LOCATION: (492)
<220> FEATURE:
<221> NAME/KEY: unsure
<222> LOCATION: (499)
<220> FEATURE:
<221> NAME/KEY: unsure
<222> LOCATION: (518)
<220> FEATURE:
<221> NAME/KEY: unsure
<222> LOCATION: (530)
<220> FEATURE:
<221> NAME/KEY: unsure
<222> LOCATION: (537)

<400> SEQUENCE: 13


gtggagccaa gtgacaggtt cttctggttt aaccgccctg gctgggtcct cttcctcatc      60

cacctcacgc tcttccagaa cgccttccag atggcgcatt tcgtttggac actgctcacc     120

ccagacctga agaaatgcta ccacgagagg ctgggcctga gcatcatgaa agttgcggtg     180
```

-continued

```
gggctggttc tccaggtcct ctgcagctac atcaccttcc cgctctacgc gctcgtcacg    240

cagatggggt cgcacatgaa gaagaccatc ttcgaggagc agacggccaa ggcggtgatg    300

aagtggcgca agacggccaa ggataaggtg cggcagcggg aggcggcagg cttcctcgac    360

gtgctgacga gcgccgacac cacgccgagc cacagccgcg cgacgtcgcc gagccggggc    420

aactcgccgg tgcacctgct ccacaagtac aggggcaggt cggaggaacc gcagagggng    480

ccggcgtcgc gngggcggng agcttcgggg aaatgtancc ggtggctgan cagcatng      538


<210> SEQ ID NO 14
<211> LENGTH: 114
<212> TYPE: PRT
<213> ORGANISM: Zea mays

<400> SEQUENCE: 14

Val Glu Pro Ser Asp Arg Phe Phe Trp Phe Asn Arg Pro Gly Trp Val
  1               5                  10                  15

Leu Phe Leu Ile His Leu Thr Leu Phe Gln Asn Ala Phe Gln Met Ala
             20                  25                  30

His Phe Val Trp Thr Leu Leu Thr Pro Asp Leu Lys Lys Cys Tyr His
         35                  40                  45

Glu Arg Leu Gly Leu Ser Ile Met Lys Val Ala Val Gly Leu Val Leu
     50                  55                  60

Gln Val Leu Cys Ser Tyr Ile Thr Phe Pro Leu Tyr Ala Leu Val Thr
 65                  70                  75                  80

Gln Met Gly Ser His Met Lys Lys Thr Ile Phe Glu Glu Gln Thr Ala
                 85                  90                  95

Lys Ala Val Met Lys Trp Arg Lys Thr Ala Lys Asp Lys Val Arg Gln
            100                 105                 110

Arg Glu


<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 15

caggttcacc cacgagactt                                                20


<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 16

ttgatgagga aagagcacga                                                20


<210> SEQ ID NO 17
<211> LENGTH: 705
<212> TYPE: DNA
<213> ORGANISM: Zea mays

<400> SEQUENCE: 17

caggttcacc cacgagactt ccttcgtgag gcagcatatg aatgtgctga acaagttccc     60

agcatcattc tacatcgtaa taagattgaa ttctaagcat cattcgatct aatatatatg    120
```

-continued

```
ctagctagct acagcaggtc gatagactga cgacgacgat catatgcaga gcaacttctt    180

ccggcagttc ttcaggtccg tgaggcaggc agactactgc gcgctgcgcc acagctttgt    240

caacgtccat ctggcccctg gcagcaagtt tgatttccag aagtacatca agcggtctct    300

ggaggatgac ttcaaggtga tcgtggggat cagtcctcct ctgtgggctt ctgctctcat    360

cttcctcttc ctcaacgtca atggtacgta cgtatacgta ggggttgttc gagatcgaga    420

tccatgcatg catcttctat ctattactat tatatgtata tacatgcatg catgcatatg    480

ctgcgtgcat gaatcatgaa tgcaggatgg cacaccatgc tctggatctc catcatgccg    540

gtggtgatca tcctgtcggt ggggacgaag ctgcagggca tcatctgccg catggcgatc    600

gacatcacgg agcgccacgc cgtcatccag ggcatcccga tggtgcaagt cagcgactcc    660

tacttctggt tcgcacgccc caccttcgtg ctctttcctc atcaa                    705


<210> SEQ ID NO 18
<211> LENGTH: 750
<212> TYPE: DNA
<213> ORGANISM: Zea mays

<400> SEQUENCE: 18

caggttcacc cacgagactt cgtttgtgag gcagcatatg aatgtgctca acaagttccc     60

agcatccttc tacatcgtaa gattcatgat gcttttctac tgaattgttg tctattgcat    120

tgcatctgac gatcgatgat gctgcctgca gagcaacttc ttccggcagt tcttcaggtc    180

cgtcaggcgg gcagactact gcgcgctgcg ccacagcttt gtcaacgtat gtagggccac    240

gccagcttgt ttgttcgttc cttcttcatt ggcaatcagc agcaacaaca atgtatgtat    300

cgtatgcagg tccatctggc ccctggcacc aagtttgatt tccaaaagta catcaagcgg    360

tctctggagg acgacttcaa ggtgatcgtg gggatcagcc ctcctttgtg ggcttctgct    420

ctcatcttcc tattcctcaa tgtcaatggt aatatatatc catcttcgtc ttcctctagc    480

ttagcttagc tagggtaata atagggtcgt ccatcatgca tctgacgacg atgcatatat    540

atatatgcag gatggcacac catgctctgg atctccatca tgccggtggt gatcatcctg    600

tccgtgggga cgaagctgca gggcatcatc tgccgcatgg cgatcgacat cacggagcgg    660

cacgccgtga tccagggcat cccgctggtg caggtcagcg actcctactt ctggttcgca    720

cgcccaacct tcgtgctctt tcctcatcaa                                     750


<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence:PCR primer

<400> SEQUENCE: 19

acattcatat gctgcctcac gaaggaa                                         27


<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence:PCR primer

<400> SEQUENCE: 20

tagctgcaga ggacctggac aacc                                            24
```

What is claimed is:

1. An isolated polynucleotide comprising:

(a) a nucleic acid sequence a polypeptide selected from the group consisting of SEQ ID NO:2, SEQ ID NO:4, SEQ ID NO:6, SEQ ID NO:8, SEQ ID NO:10, SEQ ID NO:12 and SEQ ID NO:14; [and] *or*

(b) a nucleic acid sequence that is complementary to (a).

2. A chimeric nucleic acid sequence comprising the isolated polynucleotide of claim 1 operably linked to at least one suitable regulatory sequence.

3. A transformed host cell comprising the chimeric nucleic acid sequence of claim 2.

4. A method of [altering] *reducing* the expression level of Mlo polypeptide in a host cell, the method comprising:

(a) transforming a host cell with the chimeric nucleic acid sequence of claim 2; and (b) growing the transformed host cell of step (a) under conditions suitable for expression of the chimeric nucleic acid sequence;

wherein expression of the chimeric nucleic acid sequence results in production of [altered] *reduced* Mlo polypeptide levels in the transformed host cell *increasing disease resistance*.

5. A method of obtaining an isolated polynucleotide encoding an Mlo polypeptide comprising:

(a) probing a cDNA or genomic library with at least 30 contiguous nucleotides of the isolated polynucleotide of claim 1; and (b) isolating the cDNA clone or genomic DNA clone identified in step (a);.

6. A method of obtaining an isolated polynucleotide encoding an Mlo polypeptide, the method comprising:

(a) synthesizing an oligonucleotide primer corresponding to at least 30 contiguous nucleotides of the isolated polynucleotide set forth in any of SEQ D NOs:1, 3, 5, 7, 9, 11, 13, 18 and 19; and (b) amplifying a cDNA insert present in a cloning vector using the oligonucleotide primer of step (a)

wherein the amplified isolated polynucleotide encodes an Mlo polypeptide.

7. The product of the method of claim 5.

8. The product of the method of claim 6.

9. An expression cassette comprising an isolated polynucleotide of claim 1 operably linked to a promoter.

[10. An isolated polynucleotide comprising:

(a) a first nucleic acid sequence that is at least 80% identical by the Jotun Hein method of alignment to a nucleic acid molecule encoding a polypeptide set forth in SEQ ID NO:2, SEQ ID NO:4, SEQ ID NO:6, SEQ ID NO:8, SEQ ID NO:10, SEQ ID NO:12, or SEQ ID NO:14; or (b) a second nucleic acid sequence that is complementary to the first isolated polynucleotide.]

[11. A chimeric nucleic acid sequence comprising the isolated polynucleotide of claim 10 operably linked to at leaset one suitable regulatory sequence.]

[12. A transformed host cell comprising the chimeric nucleic acid sequence of claim 11.]

[13. A method of altering the expression level of Mlo polypeptide in a host cell, comprising:

(a) transforming a host cell with the chimeric nucleic acid sequence of claim 11; and (b) growing the transformed host cell of step (a) under conditions that are suitable for expression of the chimeric nucleic acid sequence, wherein expression of the chimeric nucleic acid sequence results in altered Mlo polypeptide levels in the transformed host cell.]

14. A method for producing a transgenic plant, comprising:

(a) transforming a plant cell with an expression cassette of claim 9; and (b) regenerating the transformed plant cell of (a) to produce a transgenic plant.

15. An isolated polynucleotide as set forth in SEQ ID NOs:1, 3, 5, 7, 9, 11, or 13.

* * * * *